United States Patent [19]

Bru et al.

[11] Patent Number: 5,437,874
[45] Date of Patent: Aug. 1, 1995

[54] PHARMACEUTICAL COMPOSITION FOR THE PREPARATION OF A STABLE POWDER CONTAINING AN ASSOCIATION OF ACETYLSALICYLIC ACID AND METOCLOPRAMIDE AS THE ACTIVE INGREDIENTS

[75] Inventors: Nicole Bru, Paris; Jean-Francois S. Cordoliani, Layrac; Pierre-André Poly, Athis Mons; Jehan-Yves P. Drouin, Verrieres le Buisson, all of France

[73] Assignee: Laboratoires UPSA, Agen, France

[21] Appl. No.: 177,316

[22] Filed: Jan. 4, 1994

[30] Foreign Application Priority Data

Nov. 26, 1993 [FR] France ................. 93 14170

[51] Int. Cl.⁶ .................. A61K 9/14; A61K 9/48; A61K 31/60; A61K 31/165
[52] U.S. Cl. .................. 424/466; 424/452; 424/489; 514/159
[58] Field of Search ............ 424/452, 466, 489

[56] References Cited

U.S. PATENT DOCUMENTS

| | | | |
|---|---|---|---|
| 4,325,971 | 4/1982 | Poyser et al. | 424/324 |
| 4,380,540 | 4/1983 | Poyser et al. | 424/233 |
| 5,273,759 | 12/1983 | Simmons | 424/465 |
| 5,306,506 | 4/1994 | Zema et al. | 424/466 |

*Primary Examiner*—Gollamudi S. Kishore
*Assistant Examiner*—James M. Spear
*Attorney, Agent, or Firm*—Dennison, Meserole, Pollack & Scheiner

[57] ABSTRACT

A novel pharmaceutical composition for the preparation of a stable powder containing an association of acetylsalicylic acid and metoclopramide as the active ingredients. The acetylsalicylic acid is in the form of a water soluble salt or complex and is in association with metoclopramide or a pharmaceutically acceptable salt thereof and at least one pharmaceutically acceptable hydrophilic polymer in an amount sufficient to stabilize the metoclopramide. This composition has remarkable stability in powder form and can be used to prepare sachets for the treatment of migraine.

20 Claims, No Drawings

PHARMACEUTICAL COMPOSITION FOR THE PREPARATION OF A STABLE POWDER CONTAINING AN ASSOCIATION OF ACETYLSALICYLIC ACID AND METOCLOPRAMIDE AS THE ACTIVE INGREDIENTS

The present invention relates to a novel pharmaceutical composition containing, as the active ingredient, an association of a water-soluble salt or complex of acetylsalicylic acid and metoclopramide or one of its pharmaceutically acceptable salts.

The invention is applicable especially to the preparation of a drug for the treatment of migraine, which takes the form of effervescent or non-effervescent powders.

Migraine is a benign complaint affecting 5 to 25% of the adult population and is characterized by repeat attacks of headache which are unilateral and very often associated with nausea and vomiting, considerably increasing the discomfort due to the headaches.

Acetylsalicylic acid, a non-steroidal anti-inflammatory, is one of a range of anti-migraine treatments by virtue of its analgesic properties.

However, several pharmacokinetic studies have demonstrated that, during the migraine attack, there is a delay in the absorption of acetylsalicylic acid due to a gastric stasis, and a decrease in the amount of acetylsalicylic acid absorbed.

The administration of metoclopramide or 4-amino-5-chloro-2-methoxy-N-($\beta$-diethylaminoethyl)benzamide, in association with acetylsalicylic acid has enabled this problem to be overcome.

It has in fact been found that metoclopramide, a dopaminergic antagonist having an antiemetic activity, acts on the gastric stasis and the slowing-down of the gastric evacuation, these phenomena being responsible for the decrease in the rate of absorption of acetylsalicylic acid and characterizing migraine attacks.

This association of acetylsalicylic acid and metoclopramide has formed the subject of numerous studies and has resulted in the marketing of a tablet known under the name of MIGRAVESS®, especially in the United Kingdom.

At the present time, however, an association of 05 acetylsalicylic acid and metoclopramide is not available in powder form.

The present inventors have discovered that the pulverulent forms containing an association of acetylsalicylic acid and metoclopramide are unstable and result especially in the formation of N-acetylmetoclopramide.

Under these conditions, the object of the present invention is to solve the technical problem which consists in the provision of a novel pharmaceutical composition for the preparation of a stable powder containing an association of acetylsalicylic acid and metoclopramide as the active ingredient.

The studies undertaken have shown that it is possible to produce a pharmaceutical composition which meets this objective:

on the one hand by using the acetylsalicylic acid in the form of a soluble salt or complex, and on the other hand by adding to this association at least one hydrophilic polymer in a sufficient amount to stabilize the metoclopramide.

Thus, according to a first feature, the present invention relates to a pharmaceutical composition for the preparation of a powder, said composition comprising, as the active ingredient, an effective amount of a water-soluble salt or complex of acetylsalicylic acid in association with metoclopramide or one of its pharmaceutically acceptable salts, and at least one pharmaceutically acceptable hydrophilic polymer in a sufficient amount to stabilize the metoclopramide Within the framework of the present invention, it is possible to use a variety of water-soluble salts or complexes of acetylsalicylic acid, for example carbasalate calcium;
lysine acetylsalicylate;
sodium acetylsalicylate.

However, the best results have been obtained with carbasalate calcium.

This compound is a precursor complex of acetylsalicylic acid comprising two molecules of acetylsalicylic acid stabilized by one molecule of urea and one atom of calcium.

This compound has been perfectly described in the state of the art (MERCK INDEX 11th Edition, p. 250).

Likewise, within the framework of the present invention, it is possible to use a variety of pharmaceutically acceptable hydrophilic polymers, for example polyvidone, cellulose derivatives (hydroxypropyl cellulose, hydroxypropyl methyl cellulose, hydroxyethyl cellulose, carboxymethyl cellulose) and xanthan gum.

The best results have been obtained using polyvidone, or polyvinylpyrrolidone, as the hydrophilic polymer.

The metoclopramide forming part of the composition according to the present invention will generally be in the free form or in the form of the dihydrochloride or monohydrochloride.

The best results have been obtained using metoclopramide monohydrochloride.

The powders obtainable within the framework of the present invention can be effervescent or non-effervescent.

A composition according to the invention for the preparation of an effervescent powder will comprise a pharmaceutically acceptable effervescent system containing at least one organic acid and at least one substance capable of reacting with this organic acid to release carbon dioxide in the presence of a sufficient amount of water.

Examples of acids which can be used for this purpose are citric acid, fumaric acid, adipic acid, tartaric acid and mixtures of these compounds.

A particularly preferred acid is citric acid.

Alkali metal carbonates, especially sodium bicarbonate, potassium bicarbonate, sodium carbonate and potassium carbonate, and also carboxylysine, calcium carbonate and mixtures of the above-mentioned compounds, may be mentioned in particular among the substances capable of reacting with these organic acids.

Sodium bicarbonate will advantageously be used.

The relative amounts of acid and compound capable of reacting with this acid may easily be determined by those skilled in the art, according to the desired effervescent effect.

In one preferred embodiment in which the effervescent system consists of a mixture of sodium bicarbonate and citric acid, the relative proportions by weight of these compounds in the effervescent system will be between 20:80 and 80:20.

According to one particular characteristic of the invention, this composition also comprises an effective amount of at least one internal dehydrating agent.

The presence of an internal dehydrating agent in this composition makes it possible to enhance the stability of the powder which can be prepared from this composition.

The function of the internal dehydrating agent is to trap native traces of water or traces of water which may appear in the powder during the preparation or storage of the product.

Magnesium citrate or disodium carbonate will advantageously be used as the internal dehydrating agent.

According to another particular characteristic of the invention, this composition also comprises a pharmaceutically acceptable diluent.

This diluent again plays a favorable role in stabilizing the powders which can be prepared from these compositions.

Any pharmaceutically acceptable diluent can be used within the framework of the present invention, in particular sucrose, dextrose, mannitol, sorbitol, xylitol or lactose.

Lactose will advantageously be used as the diluent.

The respective amounts of the various constituents of the composition according to the present invention may easily be determined by those skilled in the art and depend of course on the desired final pharmaceutical form.

In general, a composition according to the present invention for the preparation of an effervescent or non-effervescent powder can contain the following, expressed in parts by weight per 10 parts of metoclopramide or one of its pharmaceutically acceptable salts:

water-soluble salt or complex of acetylsalicylic acid in an amount equivalent to 100 to 1000 parts by weight of acetylsalicylic acid;
from 2 to 15 parts by weight of hydrophilic polymer;
and if appropriate:
from 50 to 400 parts by weight of internal dehydrating agent;
from 50 to 600 parts by weight of effervescent system;
from 500 to 2500 parts by weight of diluent.

A preferred composition comprises the following, expressed in parts by weight per 10 parts of metoclopramide or one of its pharmaceutically acceptable salts:

water-soluble salt or complex of acetylsalicylic acid in an amount equivalent to 800 to 1000 parts by weight of acetylsalicylic acid;
from 2 to 10 parts by weight of polyvidone;
and if appropriate:
from 70 to 180 parts by weight of internal dehydrating agent;
from 200 to 500 parts by weight of effervescent system;
from 750 to 1750 parts by weight of diluent.

One particularly preferred composition comprises the following, expressed by weight per 10 parts of metoclopramide or one of its pharmaceutically acceptable salts:

water-soluble salt or complex of acetylsalicylic acid in an amount equivalent to 900 parts by weight of acetylsalicylic acid;
5 parts by weight of polyvidone;
and if appropriate:
180 parts by weight of internal dehydrating agent;
from 200 to 400 parts by weight of effervescent system;
1500 parts by weight of diluent.

According to a second feature, the present invention relates to a pharmaceutical preparation in the form of an effervescent or non-effervescent powder, said preparation containing a composition as defined above, optionally associated with at least one customary additive selected from sweeteners, flavorings, colors and lubricants.

The choice of these additives and their respective amounts may easily be determined by those skilled in the art.

A sweetener can be a natural sugar, for example sucrose or sorbitol, or else a synthetic product, for example saccharin or aspartame.

A currently preferred sweetener is aspartame.

A currently preferred flavoring is artificial vanilla flavoring.

Of course, any other known pharmaceutically acceptable flavoring can be used within the framework of the invention.

A currently preferred lubricant is potassium benzoate.

Of course, any other known pharmaceutically acceptable lubricant can be used within the framework of the invention.

According to one particular characteristic, a pharmaceutical preparation according to the present invention will be in the form of a powder containing an amount of composition as defined above corresponding to 5 mg, 10 mg or 30 mg of metoclopramide per dosage unit.

According to a third feature, the present invention relates to a process for the manufacture of a pharmaceutical preparation in the form of an effervescent or non-effervescent powder, said process comprising:

a) treating the metoclopramide or one of its pharmaceutically acceptable salts with an effective amount of at least one hydrophilic polymer, preferably by the mixing of powders and granulation;
b) premixing the water-soluble salt or complex of acetylsalicylic acid and at least part of the other constituents of the pharmaceutical form, preferably in the form of powders;
c) if appropriate, granulating the premix resulting from step b) and any constituents of the pharmaceutical form which have not yet been incorporated;
d) mixing the products resulting from steps a) and b) or c) and any constituents of the pharmaceutical form which have not yet been incorporated; and if appropriate
e) distributing the powder obtained at the end of step d) into sachets.

Advantageously, the treatment of the metoclopramide or one of its pharmaceutically acceptable salts with the hydrophilic polymer will be carried out by granulating a pulverulent mixture of these two constituents with an appropriate solvent.

Such a solvent can be water, alcohol, dichloromethane, isopropanol or a mixture of two or more of these compounds.

One variant can consist in spraying a solution of hydrophilic polymer in the appropriate solvent on to the metoclopramide or one of its pharmaceutically acceptable salts in powder form.

The granulation described in step c) mentioned above is preferably carried out by dry compaction, but can also be carried out by a wet granulation technique in an appropriate solvent, such as the technique conventionally employed in the pharmaceutical industry, in particular using a planetary mixer, a vacuum mixer-granulator, a fluidized bed, a dry mixer or a turbine.

It should be pointed out that, in this step, the effervescent system can be incorporated directly in the form of granules.

It should also be pointed out that some of the constituents of the pharmaceutical form, for example the sweetener or the flavoring, can be incorporated during step b) mentioned above, in the case of dry compaction, but can also be mixed directly in step d) mentioned above.

The present invention will be illustrated by the non-limiting Examples below, in which the amounts indicated are expressed in parts by weight per 10 parts by weight of metoclopramide or one of its pharmaceutically acceptable salts.

EXAMPLE 1

STEP A: TREATMENT OF THE METOCLOPRAMIDE

A pulverulent mixture of metoclopramide hydrochloride monohydrate and polyvidone (5 parts by weight) is granulated with 7% of purified water (weight/weight).

STEP B: PREMIXING OF THE SALT OR COMPLEX OF ACETYLSALICYLIC ACID AND THE OTHER CONSTITUENTS

A premix is prepared with the following constituents:
  carbasalate calcium (amount corresponding to parts by weight of acetylsalicylic acid);
  anhydrous citric acid (168 parts by weight);
  sodium bicarbonate (232 parts by weight);
  lactose (1500 parts by weight);
  magnesium citrate (180 parts by weight);
  potassium benzoate (250 parts by weight).

STEP C: DRY COMPACTION OF THE MIXTURE RESULTING FROM STEP B
STEP D: FINAL MIXING

The products resulting from steps A and C, and the following compounds: aspartame and artificial vanilla flavoring, which are in powder form, are mixed.

STEP E: PACKAGING IN SACHETS

The mixture of powders obtained at the end of step C can be packaged directly in sachets.

EXAMPLES 2 TO 6

Effervescent or non-effervescent powders having the following compositions were prepared by the procedure described above:

What is claimed is:

1. A pharmaceutical composition for the preparation of a powder comprising, as active ingredient, an effective amount of a water-soluble salt or complex of acetylsalicylic acid in association with metoclopramide or a pharmaceutically acceptable salt thereof, and at least one pharmaceutically acceptable hydrophilic polymer in an amount sufficient to stabilize the metoclopramide.

2. A pharmaceutical composition for the preparation of a powder comprising, as active ingredient, an effective amount of water soluble carbasalate calcium in association with metoclopramide or a pharmaceutically acceptable salt thereof, and at least one hydrophilic polymer in an amount sufficient to stabilize the metoclopramide.

3. A composition according to claim 1 wherein the hydrophilic polymer is polyvidone.

4. A composition according to claim 1 comprises a which also comprises a pharmaceutically acceptable effervescent system containing at least one organic acid and at least one substance capable of reacting with this organic acid to release carbon dioxide gas.

5. A composition according to claim 1 which also comprises an effective amount of at least one internal dehydrating agent.

6. A composition according to claim 5 wherein the internal dehydrating agent is anhydrous magnesium citrate.

7. A composition according to claim 1 which also comprises a pharmaceutically acceptable diluent.

8. A composition according to claim 7 wherein the diluent is lactose.

9. A composition for the preparation of a powder which comprises, by weight per 10 parts of metoclopramide or a pharmaceutically acceptable salt thereof:
  a water-soluble salt or complex of acetylsalicylic acid in an amount equivalent to 100 to 1000 parts by weight of acetylsalicylic acid;
  from 2 to 15 parts by weight of a hydrophilic polymer;
  and optionally:
  from 50 to 400 parts by weight of an internal dehydrating agent;
  from 50 to 600 parts by weight of an effervescent system; and
  from 500 to 2500 parts by weight of a diluent.

10. A composition according to claim 9 which comprises, expressed in parts by weight per 10 parts of said

| PRODUCT | Example 2 | Example 3 | Example 4 | Example 5 | Example 6 |
| --- | --- | --- | --- | --- | --- |
| Carbasalate calcium (expressed in parts by weight of acetylsalicylic acid) | 900 | 900 | 900 | 900 | 900 |
| Metoclopramide HCl $H_2O$ (expressed in parts by weight of metoclopramide) | 10 | 10 | 10 | 10 | 10 |
| Polyvidone | 8 | 3 | 5 | 5 | 5 |
| Citric acid | — | 126 | — | 294 | 168 |
| Lactose | 1000 | 1500 | 2500 | 1750 | 900 |
| Sodium bicarbonate | — | 174 | — | 406 | 232 |
| Magnesium citrate | — | 150 | 100 | 250 | 180 |
| Potassium benzoate | 100 | 200 | 150 | 250 | 200 |
| Aspartame | 5 | 15 | — | 15 | 15 |
| Flavoring | 25 | 30 | 25 | 30 | 30 |
| Sodium saccharinate | 10 | — | 10 | — | — |
| Mannitol | 1310 | — | — | — | — |
| Tartaric acid | 160 | — | — | — | — |
| Sodium carbonate | 120 | — | — | — | — | metoclopramide or pharmaceutically acceptable salt thereof:

a water-soluble salt or complex of acetylsalicylic acid in an amount equivalent to 800 to 1000 parts by weight of acetylsalicylic acid;

from 2 to 10 parts by weight of polyvidone;

and optionally:

from 70 to 180 parts by weight of said internal dehydrating agent;

from 200 to 500 parts by weight of said effervescent system; and from 750 to 1750 parts by weight of said diluent.

11. A composition according to claim 10 which comprises, expressed in parts by weight per 10 parts of said metoclopramide or pharmaceutically acceptable salt thereof;

a water-soluble salt or complex of acetylsalicylic acid in an amount equivalent to 900 parts by weight of acetylsalicylic acid;

5 parts by weight of polyvidone;

and optionally:

180 parts by weight of said internal dehydrating agent;

from 200 to 400 parts by weight of said effervescent system; and 1500 parts by weight of said diluent.

12. A pharmaceutical preparation as defined in claim 1 associated with at least one additive selected from the group consisting of sweeteners, flavorings, colors and lubricants.

13. A pharmaceutical preparation according to claim 12 which contains an amount of composition as defined in claim 1 corresponding to 5 mg, 10 mg or 30 mg of metoclopramide per dosage unit.

14. A process for the manufacture of a pharmaceutical preparation in powder form comprising:

a) treating metoclopramide or a pharmaceutically acceptable salt thereof with an effective amount of at least one hydrophilic polymer by mixing of powders thereof and granulating;

b) premixing a water-soluble salt or complex of acetylsalicylic acid and at least one other constituent of the preparation in the form of powders thereof;

c) optionally granulating the premixed powders from step b) with further constituents of the preparation;

d) mixing the products resulting from steps a) and b) or c) and optionally further constituents of the preparation; and optionally e) distributing a powder obtained from step d) into sachets.

15. A composition according to claim 2 wherein the hydrophilic polymer is polyvidone.

16. A pharmaceutical composition in powder form comprising a mixture of an effective amount of a water soluble salt or complex of acetylsalicylic acid, an effective amount of pulverulent metoclopramide and at least one pulverulent, pharmaceutically acceptable hydrophilic polymer in an amount sufficient to stabilize the metoclopramide.

17. A composition according to claim 12, further comprising a pharmaceutically acceptable diluent.

18. A composition according to claim 12, further comprising a pharmaceutically acceptable effervescent system containing at least one organic acid and at least one substance capable of reacting with said organic acid to release carbon dioxide gas.

19. A composition according to claim 12, further comprising an effective amount of at least one internal dehydrating agent.

20. A composition according to claim 19, wherein said internal dehydrating agent is anhydrous magnesium citrate.

* * * * *